(12) United States Patent
Karlsson

(10) Patent No.: US 6,844,554 B2
(45) Date of Patent: Jan. 18, 2005

(54) METHOD AND ARRANGEMENT FOR DETERMINING THE CONCENTRATION OF A GAS COMPONENT IN A GAS MIXTURE

(75) Inventor: Kai Karlsson, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 244 days.

(21) Appl. No.: 10/185,294

(22) Filed: Jun. 28, 2002

(65) Prior Publication Data

US 2004/0000643 A1 Jan. 1, 2004

(51) Int. Cl.$^7$ .............................................. G01N 21/35
(52) U.S. Cl. .............................. 250/339.13; 250/339.01
(58) Field of Search ...................... 250/339.13, 339.01, 250/339.02, 339.07, 339.12, 345, 343; 356/437

(56) References Cited

U.S. PATENT DOCUMENTS

| | | | |
|---|---|---|---|
| 4,355,233 A | * 10/1982 | Warnke et al. | ............... 250/343 |
| 4,423,739 A | 1/1984 | Passaro et al. | |
| 5,060,505 A | * 10/1991 | Tury et al. | ................... 250/343 |
| 5,246,868 A | * 9/1993 | Busch et al. | ................. 436/101 |
| 5,900,635 A | 5/1999 | Weckstrom | |
| 5,908,789 A | * 6/1999 | Weckstrom | ................. 436/133 |
| 6,147,351 A | 11/2000 | Huiku | |
| 6,555,820 B1 | * 4/2003 | Tacke et al. | ............ 250/339.01 |

FOREIGN PATENT DOCUMENTS

| | | |
|---|---|---|
| EP | 417884 | 3/1991 |
| EP | 781988 | 7/1997 |
| EP | 1061355 | 12/2000 |
| WO | 94/24528 | 10/1994 |

\* cited by examiner

Primary Examiner—Constantine Hannaher
Assistant Examiner—Otilia Gabor
(74) Attorney, Agent, or Firm—Andrus, Sceales, Starke & Sawall, LLP (57) ABSTRACT

The invention relates to a method and an apparatus for non-dispersive analysis of gas mixtures for determining the concentration of such a first gas component in a gas mixture, whose absorbance may be influenced by other gas components of said gas mixture. The apparatus comprises a sample chamber (2) for containing the gas mixture, a radiation source (1) for transmitting radiation through the gas mixture, a first optical transmission band filter (5) with a first absorption transmission band of the first gas and a first radiation detector (4). The apparatus further comprises a second optical transmission band filter (8) with a second transmission band, which is outside the first transmission band, and a second detector (7). The concentration determining means (23) are arranged to determine the concentration of the first gas using a certain formula or formulas and using the detected intensities. The second transmission band is substantially or entirely outside the absorption bands of said first gas component and comprises a second absorption band of a certain gas component causing a distortion in the absorption band of the first gas component, the strength of the second absorption band being substantially less than the strength of the first absorption band.

38 Claims, 7 Drawing Sheets

METHOD AND ARRANGEMENT FOR DETERMINING THE CONCENTRATION OF A GAS COMPONENT IN A GAS MIXTURE

FIELD OF THE INVENTION

The invention relates in general to determining the concentration of a certain gas in a mixture of gases by non-dispersively detecting absorption of radiation. In particular the invention relates to improving the measuring accuracy when the measurement error is caused by the presence of certain other gas or gases in the gas mixture.

BACKGROUND OF THE INVENTION

In measuring the concentration of a gas by infrared technique, the method most commonly used is a non-dispersive method, i.e. a method where the absorption signal is measured through an optical transmission band filter having a transmission bandwidth typically in the same order of magnitude as the width of the spectrum band using which the concentration of the gas is studied. The measured radiation signal is in this case the integrated value of the transmissions at the different wavelengths of the transmission band.

The absorption spectrum of a gas in a molecular state consists normally of absorption bands produced by molecular vibrations and, within them, a fine structure, i.e. absorption lines, due to rotational transitions. When measured with a sufficient resolution, the absorption spectrum band of a gas consists of a large number of very narrow absorption lines. For example, carbon dioxide has a molecular vibration absorption band having a mean wavelength of 4260 nm. A more detailed analysis shows that the region is made up of more than 80 narrow absorption lines caused by rotation. The half-intensity linewidth and a relative intensity of these lines are dependent on many factors, such as temperature, self-absorption due to the long measuring path, and collisions by other molecules present in the gas mixture. In measurement signal compensation on the first two can in general easily be taken in to account by measuring the temperature and the linearization effects due to the measurement geometry on the gas concerned. On the other hand, the change, sometimes significant, due to collisions by other gas components must be taken into account specifically in order to minimize concentration errors. Changes in the half-intensity linewidth of carbon dioxide in nitrogen mixture and oxygen mixture are described in the publication APPLIED OPTICS, Vol. 25, No. 14, pp. 2434–2439, 1986: Cousin, Le Doucen, Houdeau, Boulet, Henry—"Air broadened linewidths, intensities, and spectral line shapes for $CO_2$ at 4.3 $\mu$m in the region of the AMTS instrument". The half-intensity linewidth of the carbon dioxide line (ordinal number 67) of a gas mixture at normal pressure is, in an oxygen mixture, 0.055 $cm^{-1}$ (0.10 nm) and, in a nitrogen mixture, 0.060 $cm^{-1}$ (0.11 nm) for a concentration of 5% $CO_2$. The portion of self-broadening by carbon dioxide in these figures is only approx. 0.003 $cm^{-1}$.

Polar gases such as nitrous oxide ($N_2O$) have a much greater effect on the half-intensity linewidth than nitrogen and oxygen, discussed in the above-mentioned publication. For this reason, for example, the measurement result of the amount of carbon dioxide in a patient's breathing gas is typically corrected, for example, by measuring the concentration of nitrous oxide, as described in U.S. Pat. No. 4,423,739 and by using this result computationally to correct the carbon dioxide concentration. It is known that the effect of oxygen on the measurement result of nitrogen can be corrected in a manner similar to that mentioned in said patent, although the error is smaller. It is also possible that a gas component in a gas mixture absorbs infrared radiation in the same wavelength band as that gas component, which is to be measured. In this case the disturbing gas component distorts the measurement in the similar way as do the collision broadening effect.

The concentration of a gas is proportional to the number of gas molecules at the measurement volume and pressure. The number of molecules participating in infrared absorption is retained more or less unchanged in a collision process if the conditions do not otherwise change. Only the distribution of energy is slightly changed, causing broadening of the absorption line. The absorbance value integrated across the absorption line is thus retained practically unchanged. However, by the infrared technique it is not possible to measure the absorbance directly; instead, transmission is measured. According to the Lambert-Beer law, $$T=10^{-a}$$

where T is transmission and a is absorbance, applies to one wavelength. Only linearization yields an absorbance value proportional to the concentration:

$$a=-\log T=\log(1/T).$$

Especially when the measuring is carried out non-dispersively within a certain bandwidth, the total transmission signal $T_m$ will be an integral across the spectrum range of a filter $\lambda_1-\lambda_2$:

$$T_m = \int_{\lambda_1}^{\lambda_2} F(\lambda) \cdot T(\lambda) d\lambda$$

where $F(\lambda)$ is the wavelength-dependent transmission function of the filter and $T(\lambda)$ is the wavelength-dependent transmission function of the gas sample. This signal is linearized experimentally, since the Lambert-Beer low no longer applies. The end result is usually different from the total absorbance A, which is in practice independent of the collision broadening and is an integral across the absorbances $a(\lambda)$:

$$A = \int_{\lambda_1}^{\lambda_2} F(\lambda) \cdot a(\lambda) d\lambda.$$

In fact, the size of the error in $T_m$ depends on the bandwidth of the filter. Measured using a very narrow transmission band, which is of the same order as the total width (e.g. in the order of 0.1–1.5 nm) of an individual absorption line in the absorption band, the need for correcting the collision broadening is very small or non-existing. On the other hand, if the transmission band of the filter is even narrower (e.g. less than approx. 0.05–0.5 nm) than the full width of a single absorption line being measured, the collision broadening causes a reduction of the signal corresponding to the concentration, since the absorption peak becomes lower. Such a case is reported in publication WO-94/24528, in which one absorption peak of oxygen is measured using a very narrowband laser diode. In this case, however, the Lambert-Beer law applies with respect to the laser wavelength, and after linearization the absorbance can be integrated as a function of the wavelength, so that the collision broadening can be compensated for.

If the transmission band of a filter extends over a plurality of absorption peaks, as is usually the case when measuring carbon dioxide, there is need for correction, since the concentration reading increases as the collision broadening increases, or as infrared absorption of a disturbing gas component increases. When measuring carbon dioxide in a patient's breathing air, in which for example a considerable portion of the gas mixture may be nitrous oxide, a concentration value measured and calculated in a conventional manner may be up to 15% too high, owing to the error caused by the collision broadening, as explained above.

Figure 4:
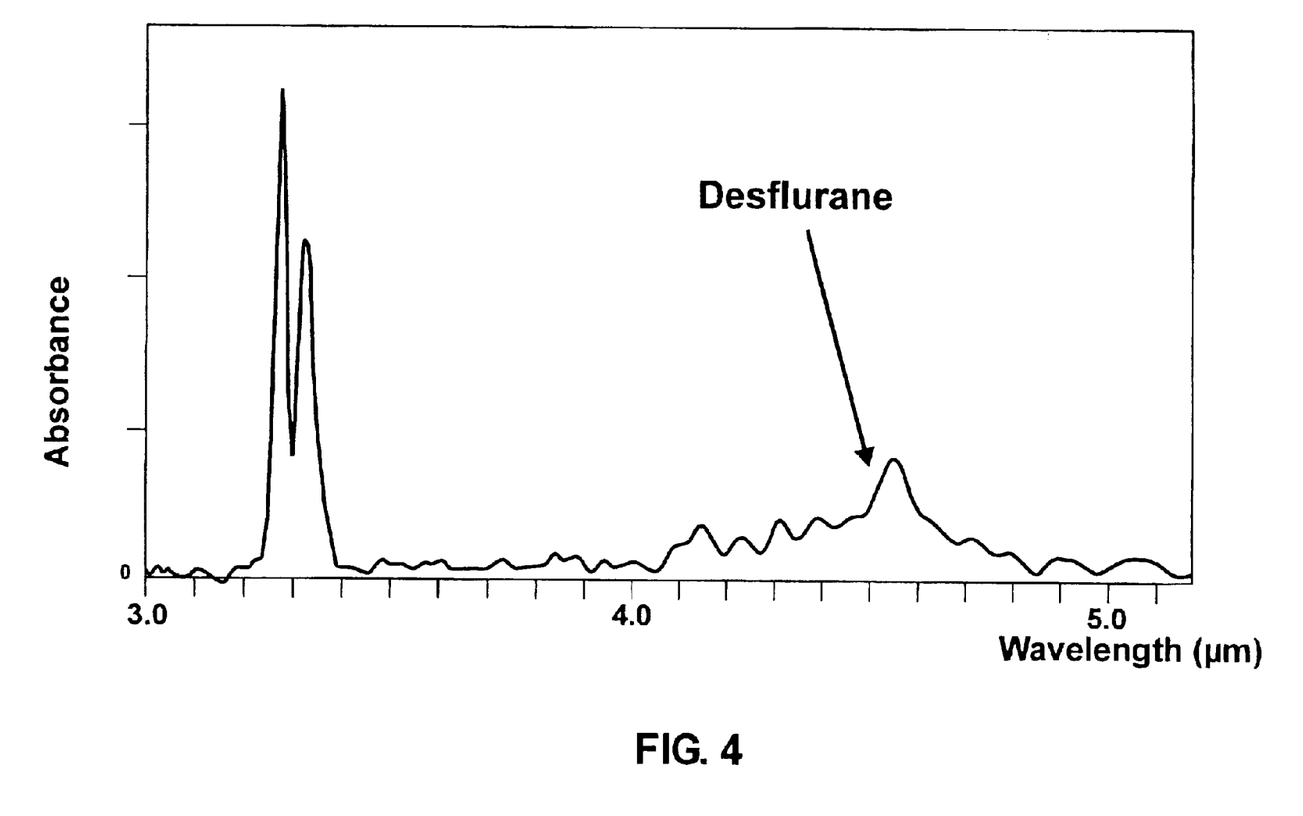
FIG. 4 presents the infrared absorbance of desflurane at the wavelength range of 3.0–5.2 $\mu$m.

It is also possible that a gas component in the gas mixture absorbs infrared radiation within the wavelength range used for the measurement of carbon dioxide. As shown in FIG. 4, anesthetic agents like for example desflurane absorb radiation in the wavelength range that is used for the measurement of $CO_2$. As a result of this, the measured $CO_2$ concentration is bigger than the real concentration, when there is desflurane present in the sample gas mixture.

Both $N_2O$ and an absorbing component like desflurane in the gas sample make a disturbing increase in the measured absorbance in the wavelength band used for $CO_2$ measurement. Thus, measurement errors caused by both of these disturbing effects can be decreased by the method according to the invention.

In a typical absorption measurement, the intensity of the transmitted radiation is measured and the transmittance can be calculated using the results. The output voltage of a radiation detector is usually proportional to the intensity of radiation arriving at the detector. To obtain as accurate results as possible the voltage V of the radiation detector has to be known usually in the following cases. Voltage $V_{dark}$ corresponds to the situation when there is no radiation arriving at the detector. Voltage $V_0$ corresponds to the situation where radiation passing a sample of gas arrives at the detector, but the concentration of carbon dioxide in the sample gas is zero. Voltage $V_c$ corresponds to the situation, where the sample gas comprises a certain concentration c of $CO_2$. When these voltages are known, the concentration c can be calculated $$c = K[\log(1/T)]^b \quad \{A\}$$

where K and b are detector-specific parameters and transmission T is calculated using the measured voltages $$T = \frac{V_c - V_{dark}}{V_0 - V_{dark}}. \quad \{B\}$$

The voltage $V_0$ may change, for example, as the radiated power of the radiation source changes, as the windows of the sample chamber get dirty or as the sensitivity of the radiation detectors changes. This voltage can be measured by inserting to the sample chamber gas, which does not contain carbon dioxide. The voltage $V_C$ is measured, when the radiation passes the gas mixture under study and when the radiation is substantially within the absorption band of the gas whose concentration is being measured. Thus, the voltage $V_C$ changes with the concentration of the gas of interest. The voltage $V_{dark}$ may change due to noise in the radiation detector or in the measurement electronics. $V_{dark}$ can be measured, for example, by preventing radiation emitted by the source from arriving the detector or by turning the radiation source off. When a thermopile detector is used as radiation detector, it can under certain conditions be assumed that $V_{dark}=0$.

The voltage $V_0$ can be measured by introducing to the sample chamber gas that does not absorb radiation at the wavelength band used for the concentration measurement. This method naturally interrupts the normal operation of the gas sensor.

It is also possible, continuously and without interrupting the operation of the gas sensor, to estimate the voltage $V_0$ by using a reference wavelength band and measuring the radiation either with a reference detector or the same detector that is used for measuring the voltage $V_C$. The reference wavelength band is in the prior art selected so that the gas mixture under study does absorb infrared radiation in that wavelength band. Thus, it can be assumed that:

$$V_0 = kV_{ref} \quad \{C\}$$

and where the parameter k can be determined, for example, by providing a gas mixture, which does not contain the studied gas in the sample chamber. In this case the transmittance T can be calculated using $$T = \frac{V_c - V_{dark}}{kV_{ref} - V_{dark}}. \quad \{D\}$$

If there is only one radiation detector in the gas sensor and the reference measurement is performed by alternatively inserting a measurement filter and a reference filter to the optical path, then the voltage may be measured, for example, when changing the filters.

The $CO_2$ concentration calculated using the above formula is not an accurate concentration, if the sample gas contains nitrous oxide or other gas components that have an effect on the measured transmittance, e.g. like collision broadening.

It is possible to correct the effect of the nitrous oxide on the carbon dioxide concentration by correcting the $CO_2$ concentration value with a constant correction term (for example, 0.5% independently of the percentage of the $CO_2$ in the gas mixture) or with a correction term that is proportional to the $CO_2$ concentration (for example, 0.1 times the estimated $CO_2$ concentration). This correction requires that the presence of $N_2O$ (nitrous oxide) in the gas mixture is known. The correction term is typically selected so that it corrects the effect of the nitrous oxide when using a certain default gas mixture, for example a mixture which contains 75% $N_2O$, 5% $CO_2$ and 20% $O_2$. The correction term typically does not depend on the concentration of $N_2O$ in the gas mixture.

The problem with this correction method is that it is exact only for the $N_2O$ concentration using which it was determined. For example, in the beginning of an anesthesia (i.e. in induction) when the dosage of $N_2O$ to the patient is started, $N_2O$ absorbs rapidly to the patient and the $N_2O$ concentration in the alveolar exhalation air of the patient is smaller than the default concentration. The use of the correction term determined using the default $N_2O$ concentration may thus cause a larger error to the estimated $CO_2$ concentration than using no correction term at all. The $CO_2$ concentration in the alveolar exhalation air of the patient is a very useful quantity that should be measured very accurately especially during the induction. If this compensation method is used it must be switched on manually or there has to be, for example, a signal from a separate $N_2O$ detection system that triggers the use of the compensation on when the concentration of $N_2O$ in the alveolar exhalation air increases a certain predetermined value.

The effect of the $N_2O$ on the measurement of carbon dioxide concentration can also be compensated by simultaneously measuring the $N_2O$ concentration in the sample gas mixture and making an $N_2O$-concentration-dependent compensation in real time. The magnitude of the compensation depends in this case on the $CO_2$ and $N_2O$ concentration.

Using this method it is possible to compensate the effect of $N_2O$ accurately enough at all $N_2O$ concentrations. The problem here is the need for a real-time measurement of the $N_2O$ concentration that is synchronized with the $CO_2$ measurement. It is possible to provide one sensor which can detect both gases or a separate sensor for each gas.

U.S. Pat. No. 4,423,739 describes a system where absorption at the sample gas is measured at three different wavelength ranges: A first bandpass reference filter is used to detect absorption at a wavelength range, where neither nitrous oxide nor carbon dioxide oxide absorbs radiation. The selected wavelength range is centered at 3.69 $\mu$m, and using this reference filter it is possible to keep track, for example, of accumulation of dirt in the sample chamber windows or of the intensity of radiation. A second bandpass filter is used to determine a measured concentration of carbon dioxide; the wavelength range of this filter is centered at 4.25 $\mu$m. A third bandpass filter is used to determine the concentration of nitrous oxide; the wavelength range of this filter is centered at 3.9 $\mu$m. The corrected carbon dioxide concentration is then determined using the concentration of nitrous oxide and the measured concentration of carbon dioxide. The system presented in U.S. Pat. No. 4,423,739 is a side-stream analyzer using a single beam configuration and one detector; the filters are placed to a rotary filter wheel in front of the detector.

The method presented in U.S. Pat. No. 4,423,739 makes the sensor complicated because three measurement wavelengths are needed, and because it is necessary to know, for example, all the gas components affecting the broadening of the absorption lines and their concentrations. Furthermore, ample experimental material must be obtained for the calculation of the corrected carbon dioxide concentration, because it involves an empirically determined constant describing the collision broadening.

U.S. Pat. No. 5,900,635 describes an alternative system for taking into account the effect of nitrous oxide on the determined concentration of carbon dioxide. This system can be implemented either in a single beam or in a multibeam configuration. Absorption related to the carbon dioxide is determined using a first detector and a bandpass filter whose wavelength range is centered at 4.25 $\mu$m. A compensation measurement is carried out by placing an additional compensation filter at the radiation path. The compensation filter is a gas container, where the gas mixture comprises carbon dioxide. The gas container is a closed container, and the size of the correction is selected by the amount of carbon dioxide in the container. The correction is thus properly selected for a certain combination of carbon dioxide and nitrous oxide.

U.S. Pat. No. 6,147,351 describes further a system, where the effect of nitrous oxide on the concentration of carbon dioxide is compensated. In this system, the absorption related to carbon dioxide is determined twice, for example, by guiding the radiation through the studied gas along two optical paths whose length is different. When the length of the optical paths are correctly chosen, the measured absorption results are linearly independent and it is possible to determine the concentration of carbon dioxide in the gas mixture and the effect of the collision broadening using certain equations. Some parameters in the equations depend on the measured absorption values and, therefore, there may be need for extensive measurements to determine the parameters before the system can be used.

As discussed above, a sensor using which it is possible to determine the concentrations of both $N_2O$ and $CO_2$ is complex and its structure, for example the dimensions of the sample chamber, is a compromise not providing the best possible measurement accuracy for either of the gases. The use of a separate $CO_2$ sensor and $N_2O$ sensor causes problems in synchronizing the measurement results and, of course, requires two sensor systems. The use of two separate sensors is especially difficult in mainstream gas sensors, where the sensor is attached to the breathing tube and the sensor has to be very small and lightweight.

SUMMARY OF THE INVENTION

The object of the invention is to provide a simple method for determining the concentration of a certain gas component in a mixture of gases using non-dispersive absorption measurement. A further object of the invention is to provide a method for determining the concentration of the gas component accurately even when the gas mixture comprises other gas or gases that cause collision broadening to the absorption band of the studied gas and even when the concentration of the other gases is not determined or known. A further object of the invention is to provide a method that can be implemented using only one sensor. A further object of the invention is to provide a method using which it is, if needed, possible to determine continuously the concentration of a gas component in a gas mixture.

The object of the invention is achieved by determining the concentration of the gas component using a first wavelength range and by selecting a second wavelength range, where the reference radiation intensity is determined, so that the reference radiation intensity decreases when the gas mixture contains a component, which decreases the radiation intensity that pass the gas sample at the first wavelength range.

A method according to the invention is a method for non-dispersive analysis of gas mixtures for determining the concentration of such a first gas component in a gas mixture, whose absorbance may be influenced by other components of said gas mixture, said method comprising the steps of: providing a radiation source emitting radiation over a wavelength range along a certain radiation path through a gas mixture; providing to said radiation path an optical first bandpass filter having a first transmission band within an absorption band of said first gas component; providing a first detector for detecting a first intensity of radiation passing along said radiation path and through said first bandpass filter, this first intensity producing a first measurement signal when the gas mixture in the radiation path is the gas mixture to be analyzed; providing to said radiation path an optical second bandpass filter having a second transmission band outside the first transmission band; and providing a second detector for detecting a second intensity of radiation passing along said radiation path and through said second bandpass filter, this second intensity producing a second measurement signal when the gas mixture in the radiation path is the gas mixture to be analyzed; determining a concentration value for the first gas component in the gas mixture to be analyzed using a predetermined formula or predetermined formulas, which take(s) as inputs at least said first measurement signal and said second measurement signal; and selecting the second transmission band so that it is substantially or entirely outside the absorption bands of said first gas component and so that it comprises a second absorption band of a certain second gas component causing a distortion in the absorption band of the first gas component, the strength of the second absorption band being substantially less than the strength of the first absorption band.

Alternatively the method is provided with the steps of: providing a radiation source emitting radiation over a wavelength range along a certain radiation path through a gas mixture; providing to said radiation path a first extension radiation path with an optical first bandpass filter having a first transmission band within an absorption band of said first gas component; providing a first detector for detecting a first intensity of radiation passing along said radiation path and said first extension radiation path, this first intensity producing a first measurement signal when the gas mixture in the radiation path is the gas mixture to be analyzed; providing to said radiation path a selective beam splitting means having a second transmission range, which comprises at least the first transmission band; providing to said radiation path a second extension radiation path with an unlimited transmission; providing a second detector for detecting a second intensity of radiation passing along said radiation path and said second extension radiation path, this second intensity producing a second measurement signal when the gas mixture in the radiation path is the gas mixture to be analyzed; determining a concentration value for the first gas component in the gas mixture to be analyzed using a predetermined formula or predetermined formulas, which take(s) as inputs at least said first measurement signal and said second measurement signal; and selecting the second transmission range so that it extends substantially or entirely outside the absorption bands of said first gas component and so that it comprises a second absorption band of a certain second gas component causing a distortion in the absorption band of said first gas component, the strength of the second absorption band being substantially less than the strength of the first absorption band.

A method according to the invention is a method for determining the concentration of a first gas component, for example carbon dioxide, in a gas mixture in a situation, where the gas mixture may contain a second gas component, for example nitrous oxide, having a collision broadening effect on the first gas component. In the method according to the invention, the intensity of light passing the gas mixture under study is measured using two separate transmission bands: the first transmission band is selected so that it is within an absorption band of the first gas component. The first measurement signal thus decreases as the concentration of the first gas component increases.

In a method according to the invention, a second transmission band is outside the absorption bands of the first gas component: the concentration of the first gas component thus does not—at least significantly—affect a second measurement signal measured using the second transmission band. It is thus possible to provide a reference gas mixture, which is free of the first gas component and of the second gas component, to the sample container and to measure the ratio of a first reference signal, measured using the first transmission band, and a second reference signal, measured using the second transmission band. This measurement is typically performed at regular intervals, but not on-line during concentration measurements. The second measurement signal, when corrected with said ratio, enables the estimation of the second reference signal without providing a reference gas mixture to the gas container.

In a method according to the invention, the presence of a gas component that may have a disturbing effect on the first gas component is taken into account by selecting the second transmission band so that a second absorption band, related to the second gas component, is within the second transmission band. The second transmission band is selected so that the absorption of the second gas component has a suitable effect on the signal from the second radiation detector. The magnitude of the changes in the second measurement signal can be varied, for example, by adjusting the width of the second transmission band.

The concentration of the first gas component is, in a method according to the invention, determined using preferably a single predetermined formula $\{A\}$, which takes as inputs at least said unprocessed first measurement signal, said unprocessed second measurement signal and the ratio k of the first reference signal and the second reference signal. A single predetermined formula refers to calculations, which do not involve matrix algebra or resolving systems of equations. The formula is such that it takes the values of the measurement signals as input. The formula can, of course, be written as series of formulas, and the result of an earlier formula can be inserted to a next formula.

When the concentration of the first gas component increases, the first measurement signal, which is measured at the first transmission band having an absorption peak related to the first gas component, decreases. The possible collision broadening causes the absorption related to the first gas component to increase, when the absorption is measured over a wavelength range that extends over a plurality of absorption lines. In the presence of a second gas component, which has a collision broadening effect on the first gas component, the first measurement signal is smaller than for the same concentration of the first gas component in the absence of the second gas component. The main idea in a method according to the invention is that the second measurement signal, measured using the second transmission band, decreases as the concentration of the second gas component increases, because the second gas component causes weak absorption band at the second transmission band. The presence of the second gas component thus causes both the first and second measurement signals to decrease. In a method according to the invention, the second measurement signal thus cancels out at least partly the effect of collision broadening at the first measurement signal.

The main advantage of the invention is that the size of the correction caused by the second measurement signal on the concentration of the first gas component depends automatically on the concentration of the second gas component in the gas mixture to be analyzed. The larger the concentration of the second gas component, the larger the correction caused by the second measurement signal. There is thus no need, for example, to turn the correction on or off depending on the estimated concentration of the second gas component. This is the case for some collision broadening corrections.

The magnitude of the correction caused by the second measurement signal typically depends on the concentration of the first gas component and the second gas component. The width of the second transmission band is selected so that for a typical composition of the gas mixture, called below a calibration gas mixture, the determined concentration of the first gas components correct. For other compositions of the gas mixture to be analyzed, the correction caused by the second measurement signal is typically to the right direction, but no necessarily of the right size.

A second advantage of the invention is that a measurement arrangement according to the invention needs only two transmission bands at which absorption caused by the gas mixture is determined. There is no need, for example, to determine absorption at a third transmission band. Typically measurement arrangements designed for non-dispersive analysis of gas mixtures are designed for determining absorption at least at one measurement transmission band and at a reference transmission band. The reference transmission band can, typically in any measurement arrangement, selected according to the invention. A measurement arrangement according to the invention is especially adaptable in mainstream gas sensors, where the sensor is attached to the breathing tube and the sensor has to be very small and lightweight.

A further advantage of the invention is that there is no need to determine the concentration of the second gas component for determining the concentration of the first gas component. Especially in patient monitoring applications, where for example the concentration of nitrous oxide is an important patient monitoring parameter, the accuracy of a determined concentration typically has to be guaranteed in any situation. Furthermore, to determine the concentration of the nitrous oxide in addition to carbon dioxide, an absorption measurement at a third transmission band is required.

The invention relates also to an apparatus for providing an indication of the concentration of a first gas in a mixture of gases, said apparatus employing non-dispersive absorption of radiation and comprising: a sample chamber for containing the gas mixture; a radiation source means for transmitting radiation through the gas mixture; a first optical transmission band filter and first radiation detector means for detecting the intensity of the radiation exiting the sample chamber at a first transmission band, which comprises a first absorption spectrum band of the first gas; a second optical transmission band filter and second detector means for detecting the intensity of the radiation exiting the sample chamber at a second transmission band, which is outside the first transmission band; and concentration determining means, which are arranged to determine the concentration of the first gas in the gas mixture using a certain concentration formula and using the detected intensity of the radiation at the first transmission band and at the second transmission band, whereupon the second transmission band is substantially or entirely outside the absorption bands of said first gas component and comprises a second absorption band of a certain gas component causing a distortion in the absorption band of the first gas component, the strength of the second absorption band being substantially less than the strength of the first absorption band.

An apparatus according the invention may alternatively comprise: a sample chamber for containing the gas mixture; a radiation source means for transmitting radiation through the gas mixture; first radiation detector means for detecting the intensity of the radiation exiting the sample chamber at a first wavelength range, which comprises a first absorption spectrum band of the first gas; second detector means for detecting the intensity of the radiation exiting the sample chamber at a second wavelength range, which is substantially or entirely outside the first wavelength range; an optical transmission band filter, whose transmission band is one of the first and second wavelength ranges; concentration determination means, which are arranged to determine the concentration of the first gas in the gas mixture using a certain concentration formula and using the detected intensity of the radiation at the first wavelength range and at the second wavelength range; an optical blocking range filter, whose blocking range comprises at least the other of the first and second wavelength ranges and which is arranged at a certain angle so that it operates as a beam splitter reflecting radiation at the blocking range to one of the radiation detector means and transmitting radiation at least at the transmission band towards the other radiation detection means, and the second wavelength range is substantially outside the absorption bands of said first gas component and so that it comprises a second absorption band of a certain gas component causing a distortion in the absorption band of the first gas component, the strength of the second absorption band being substantially less than the strength of the first absorption band.

BRIEF DESCRIPTION OF THE DRAWINGS

In the accompanying drawings, preferred embodiments of the invention and preferred methods of practicing the invention are illustrated, in which.

DESCRIPTION OF THE PREFERRED EMBODIMENTS

Figure 1:
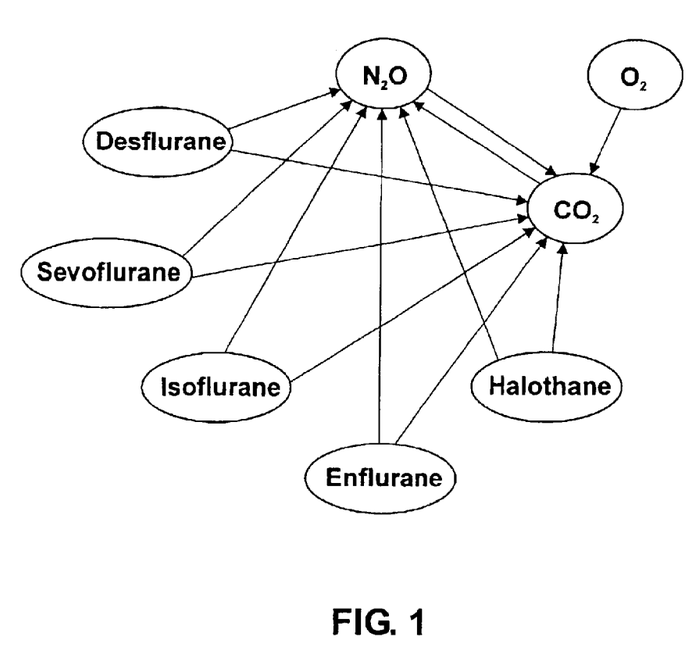
FIG. 1 illustrates the collision broadening effect of various anesthesia gases on each other.

In the figures the same reference numerals are used for same or analogous parts. FIG. 1 presents the typical effects of various anesthesia gases on each other. As can be seen in FIG. 1, practically all gas components present in breathing gas affect the carbon dioxide measurement, when infrared absorption is measured non-dispersively using an optical bandpass filter, whose transmission band extends over a plurality of absorption lines. Carbon dioxide requires most compensation: in addition to nitrous oxide ($N_2O$) oxygen ($O_2$), desflurane (Des), sevoflurane (Sev), isoflurane (Iso), enflurane (Enf), and halothane (Hal) have a disturbing effect to the carbon dioxide measurement.

Figure 2:
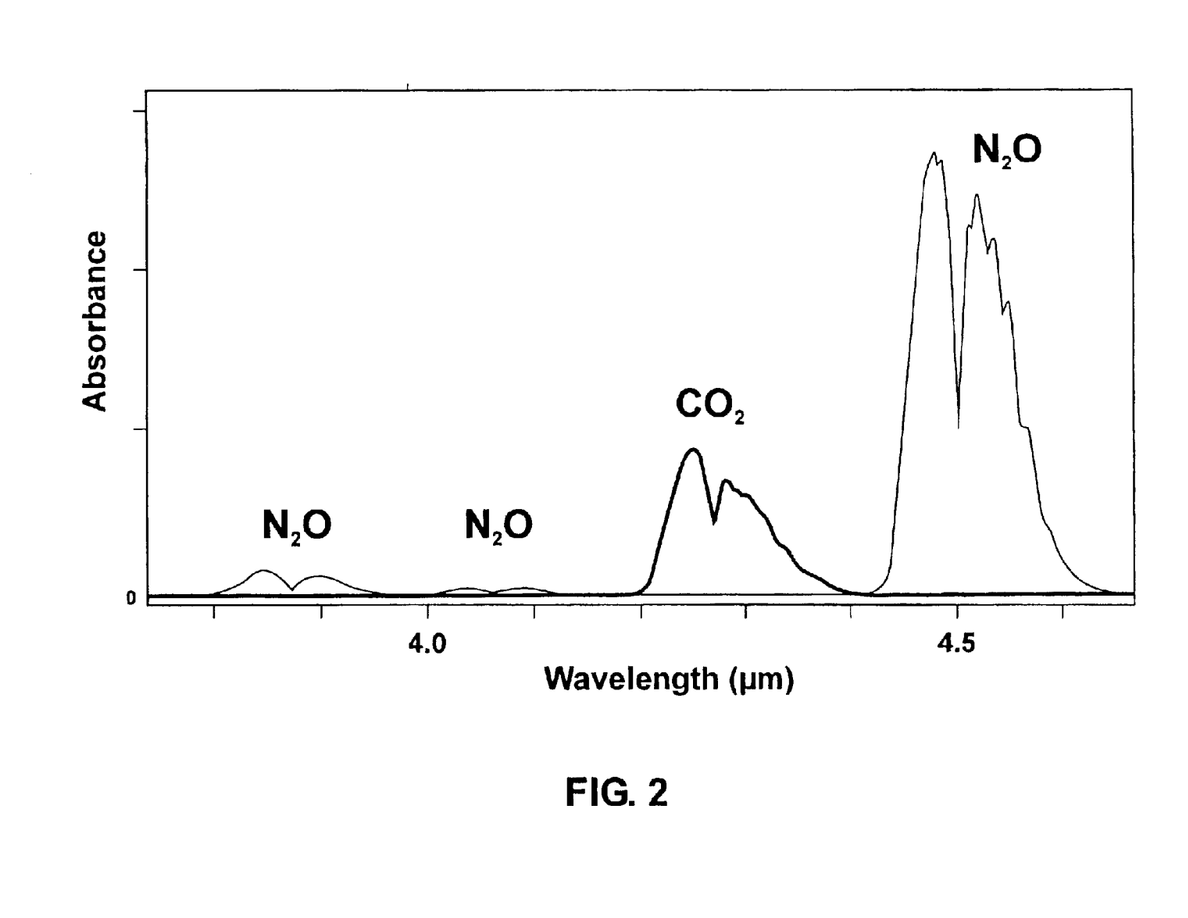
FIG. 2 presents the infrared absorbance of nitrous oxide and carbon dioxide at the wavelength range of 3.5–4.7 $\mu$m.

In a first preferred embodiment of the invention, the collision broadening caused by nitrous oxide on the carbon dioxide is corrected. FIG. 2 shows infrared absorbance of carbon dioxide (solid line) and nitrous oxide (light line) as functions of the wavelength of infrared radiation. Carbon dioxide has an absorption band at the wavelength range 4.2–4.4 $\mu$m, and this is typically the wavelength range at which absorption related to carbon dioxide is measured. Nitrous oxide has various absorption bands, and FIG. 2 presents three of them: a strong absorption band at 4.4–4.65 $\mu$m, a weaker absorption band at 3.8–3.95 $\mu$m and a very weak absorption band at 4.0–4.15 $\mu$m. The strong absorption band of nitrous oxide at 4.4–4.65 $\mu$m is stronger than the absorption band of carbon dioxide. In addition, the concentration of nitrous oxide is typically 70% of breathing air during anesthesia.

As shown in FIG. 2, $N_2O$ does not absorb radiation between 3.5 $\mu$m and 3.8 $\mu$m. Thus, it is possible to control the effect of $N_2O$ on the second reference signal by selecting the width of the second wavelength band. The effect of $N_2O$ to the reference signal is maximal when the second wavelength band is entirely between 3.8 μm and 3.9 μm. The effect of $N_2O$ to the reference signal can be decreased by expanding the second wavelength band to the wavelength range where $N_2O$ does not have absorption. The second wavelength band can be expanded towards shorter or longer wavelengths. The second wavelength band can even partially overlap with the absorption band of $CO_2$ as long as it is substantially outside the first wavelength band and is selected so that it decreases the disturbing effect caused by $N_2O$.

Selection of the wavelength band for the measurement of the reference signal can for example be done so that the effect of collision broadening is cancelled at a clinically relevant gas mixture containing 5% $CO_2$ and 70% $N_2O$. As an example, measurement results obtained when the measuring wavelength band is from 4.3 μm to 4.4 μm and the reference wavelength band is from 3.5 μm to 4.0 μm are shown in table 1.

As can be seen, the $CO_2$ concentration is correctly measured when the gas does not contain $CO_2$. At 70% $N_2O$ and no $CO_2$, the measured $CO_2$ concentration is slightly negative and may thus be rounded to 0.00 because negative concentrations do not exist. At 5% $CO_2$+70% $N_2O$, the measured $CO_2$ concentration is 4.96%. If the reference signal had been measured according to prior art without any absorption in the reference band by $N_2O$, the measured $CO_2$ concentration would have been 5.57%.

Typically the length of the optical path in the gas mixture to be analyzed is a few millimeters, when the measurement equipment is designed for measurement of nitrous oxide using wavelength range 4.4–4.65 μm, and a few tens of millimeters, when designed for measurement of carbon dioxide using wavelength range 4.2–4.4 μm. Absorption related to the nitrous oxide can thus be saturated at the wavelength range of 4.4–4.65 μm, if the length of the sample gas container is designed for the measurement of carbon dioxide. The weaker absorption band at 3.8–3.95 μm is suitable for correcting the effect of collision broadening according to the invention.

The weak absorption band at 4.0–4.15 μm may also be used, but changes in the intensity of infrared radiation may be very small at this wavelength range when the sample gas container is designed for measurement of carbon dioxide. The first wavelength range in a method according to the first preferred embodiment of the invention thus typically covers part of the wavelength range 4.2–4.4 μm and the second wavelength range may extend, for example, from 3.5 μm to 4.0 μm.

As can be seen from FIG. 4, anesthetic agents like for example desflurane have an absorption band in the 3.3 m wavelength range. This wavelength range can be included to the second wavelength band according to the invention for decreasing the disturbing effect of the absorption of radiation by anesthetic agents within the first wavelength band for measuring the $CO_2$ concentration.

Figure 3:
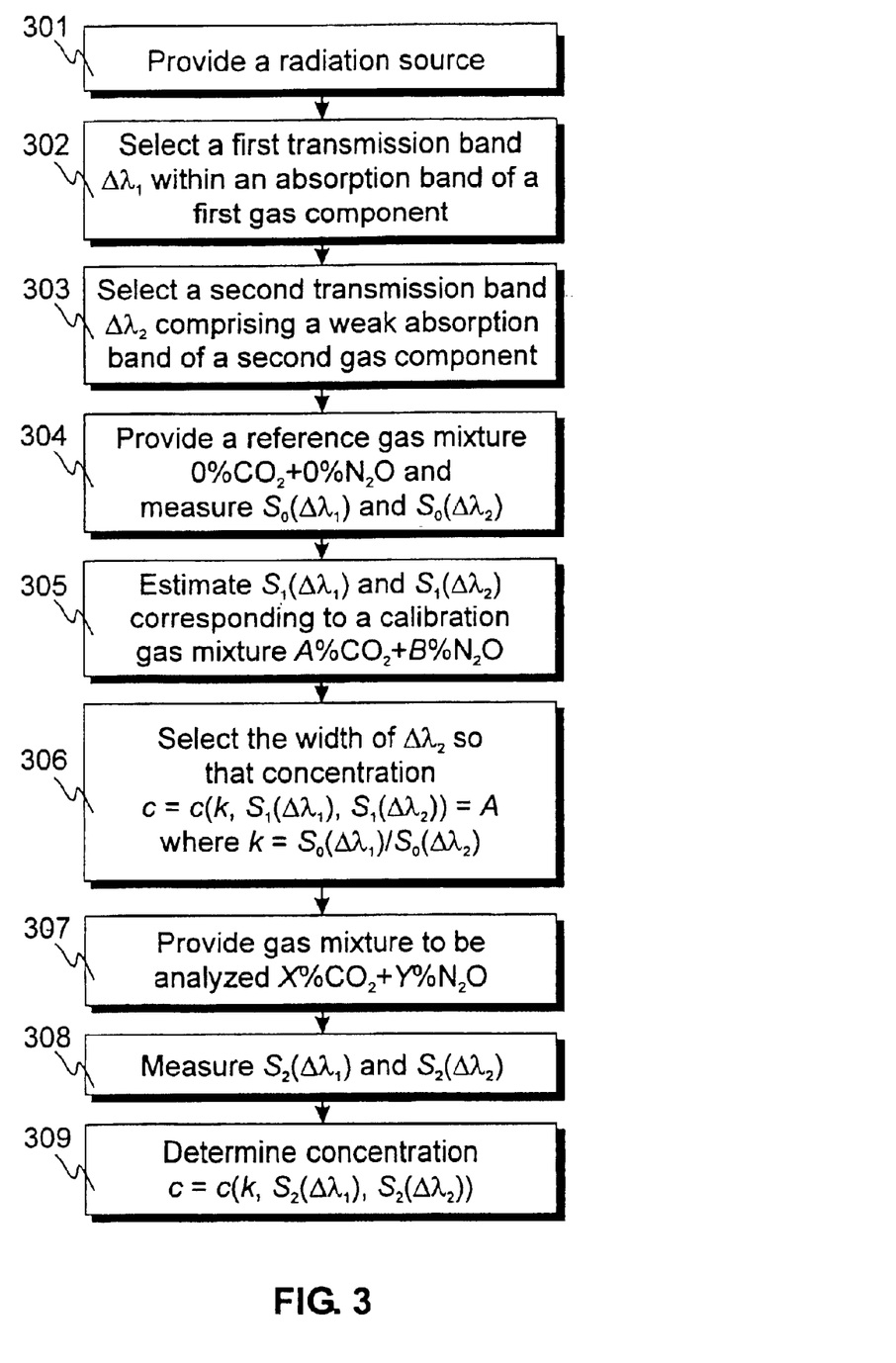
FIG. 3 illustrates a flowchart of a method according to a second preferred embodiment of the invention.

FIG. 3 presents a flowchart of a method 300 according to a second preferred embodiment of the invention. As an example, carbon dioxide is treated as the first gas component and nitrous oxide as the second gas component. In step 301 a radiation source emitting radiation at a certain wavelength range is provided. This radiation travels through a gas mixture to be analyzed along a certain radiation path, and the length of the radiation path is typically determined so that the absorption related to the first gas component can be reliably determined. For carbon dioxide, for example, the length of the radiation path in the gas mixture is typically between 3 mm and 6 mm. In step 302 a first transmission band $\Delta\lambda_1$, at which the changes in the intensity of radiation are detected, is selected. As discussed above, for carbon dioxide this transmission band is typically centered at 4.27 μm and its width is about 80 nm –100 nm (full-width-at-half-maximum, defined using the transmission curve of a filter).

In step 303 the second transmission band $\Delta\lambda_2$ is selected according to the invention. This transmission band is separate from the first transmission band and it comprises an absorption band related to the second gas component, the absorption band being weaker than the absorption band related to the first gas component. As discussed above, for nitrous oxide this second transmission band may be 3.5–4.0 μm.

In step 304 a reference gas mixture, which is free of the first gas component, is provided and the intensity of the radiation at the first transmission band $S_0(\Delta\lambda_1)$ and at the second transmission band $S_0(\Delta\lambda_2)$ is determined. Using these signals it is possible to estimate a ratio k, $$k = \frac{S_0(\Delta\lambda_1)}{S_0(\Delta\lambda_2)}, \quad \{E\}$$

which is used in determining the concentration of the first gas component in a gas mixture. This step can be performed preferably only during the manufacturing of the gas sensor. In order to take any changes in the sensor optics or detector sensitivity into account, this step can also be made at certain intervals by the user of the gas sensor as part of the sensor's maintenance.

In step 305 a first and second calibration signals $S_1(\Delta\lambda_1)$ and $S_1(\Delta\lambda_2)$ corresponding to the gas mixture A% $CO_2$+B% $N_2O$ are estimated. These calibration signals correspond to radiation passing a calibration gas mixture having a certain concentration A of the first gas component and a certain second concentration B of the second gas component and the intensity of radiation is determined at the first transmission band (first calibration signal) and at the second transmission band (second calibration signal). The signals can be estimated, for example, using the information about the intensity distribution of the radiation emitted by the radiation source and about the absorbance of the first and second gas components. This step is taken during the development of the gas sensor in order to specify the suitable wavelength bands $d(\Delta\lambda_1)$ and $d(\Delta\lambda_2)$ for the sensor.

In step 306 the width of the second transmission band is selected so that the concentration of first gas component in the calibration gas mixture, estimated using a certain formula $c=c(k, S_1(\Delta\lambda_1), S_1(\Delta\lambda_2))$, is the concentration of the first gas component in the calibration gas mixture. After the second transmission band has been selected properly, the actual analysis of gas mixtures is performed in steps 307-309. In the measurements, a gas mixture to be analyzed is provided on the radiation path (step 309) and a first and second measurement signals $S_2(\Delta\lambda_1)$ and $S_2(\Delta\lambda_2)$ are measured in step 310. The concentration of the first gas component in the gas mixture to be analyzed is determined in step 311 using the same formula and the measurement signals: $c=c(k, S_2(\Delta\lambda_1), S_2(\Delta\lambda_2))$. Steps 306, 307 and 308 describe the normal operation of the gas sensor according to the invention. Thus, it is obvious that in normal operation, steps from 300 to 305 need not be performed and the gas sensor is able to measure the desired gas concentration by only measuring signals S1 and S2 and then calculating the gas concentration using a single formula.

Let us consider an example, which shows that the selecting the second transmission band according to the invention produces more correct concentrations of the first gas component than a conventional choice of the second transmission band. There is no absorption related to the second gas component in the conventionally selected second transmission band. If the gas mixture to be analyzed contains typically 5% of carbon dioxide and 70% of nitrous oxide, then the second transmission band should be determined so that the error in $CO_2$, the measured $CO_2$ concentration is minimized for that mixture.

Consider that a certain first transmission band has been selected. To determine the effect of the collision broadening caused by 70% of nitrous oxide measurement signals $S_1(\Delta\lambda_1)$ corresponding to the intensity of radiation at the first transmission band in a first 5% $CO_2$+0% $N_2O$ calibration gas mixture and in a second 5% $CO_2$+70% $N_2O$ calibration gas mixture are measured. The result is that the effect of the collision broadening is −2% in this example. The concentration of carbon dioxide in a gas mixture, expressed in percentage, is calculated using the formula:

$$c = -125 \cdot |\log(1/T)|^{1.43}$$

where $$T = \frac{S_1(\Delta\lambda_1)}{kS_1(\Delta\lambda_2)}.$$

The ratio k is related to a reference gas, and it is not affected by the nitrous oxide concentration. The concentration of the carbon dioxide remains unaffected, when the second measurement signal $S_1(\Delta\lambda_2)$ also changes by −2%, when the concentration of nitrous oxide increases from 0% to 70% in a gas mixture. It is known that a gas mixture having 70% of nitrous oxide absorbs about 10% of radiation at the wavelength range 3.85–3.95 μm, when the radiation path in the gas mixture is about 3.4 mm long. To obtain a decrease of 2% to the second measurement signal $S_1(\Delta\lambda_2)$, the second transmission band can thus be selected to be five times broader: 3.5–4.0 μm. To check that the selected second transmission band work properly, a second measurement signal corresponding to a 0% $CO_2$+70% $N_2O$ third calibration gas is measured and the result is 9800 μV. A second measurement signal corresponding to a 0% $CO_2$+0% $N_2O$ reference gas is 10 000 μV. The desired decrease of 2% is thus obtained.

Table 1 presents all the measured signals and the determined carbon dioxide concentration for each gas mixture, when the second transmission band is selected according to the invention.

TABLE 1

Measured signals and determined carbon dioxide concentrations.

| Gas mixture | $S_1(\Delta\lambda_1)$ | $S_1(\Delta\lambda_2)$ | $c(CO_2)$ |
|---|---|---|---|
| 0% $CO_2$ + 0% $N_2O$ | 10000 μV | 8000 μV | 0.00% |
| 0% $CO_2$ + 70% $N_2O$ | 10000 μV | 7860 μV | −0.14% |
| 5% $CO_2$ + 70% $N_2O$ | 7700 μV | 7860 μV | 4.96% |
| 5% $CO_2$ + 0% $N_2O$ | 7850 μV | 8000 μV | 5.00% |

As can be seen, the ratio k between the measurement signals when there is no $CO_2$ and no $N_2O$ in the gas sample is 10000/8000=1.25. Consequently, the calculated concentration of the carbon dioxide in the reference gas is zero.

Because the value of the coefficient k is now known, it is possible to calculate the carbon dioxide concentrations in the other gas mixtures. The measured carbon dioxide concentration in the 0% $CO_2$+70% $N_2O$ gas mixture is very near zero. The absorption related to nitrous oxide on the second transmission band distorts the concentration reading slightly. The measured carbon dioxide concentration in the gas mixture 5% $CO_2$+70% $N_2O$ is 4.96%, which is also very near the correct value. This gas mixture is the gas mixture, for which the size of the correction is determined. The carbon dioxide concentration in the 5% $CO_2$+0% $N_2O$ gas mixture is correctly determined.

To compare the above results with a carbon dioxide concentration determined using a second transmission band, where there is no absorption related to nitrous oxide, it can be assumed that the second measurement signal is 8000 μV also for the 5% $CO_2$+70% $N_2O$ gas mixture. The resulting carbon dioxide concentration is 5.57%. The error in this reading is more than 10%.

The method according the invention can be used, for example, for determining the concentration of carbon dioxide in a gas mixture comprising the respiration air of a subject, who is typically a patient. Furthermore, a method according to the invention can be used for determining the concentration of carbon dioxide in a gas mixture comprising the alveolar exhalation air of the subject.

Figure 5:
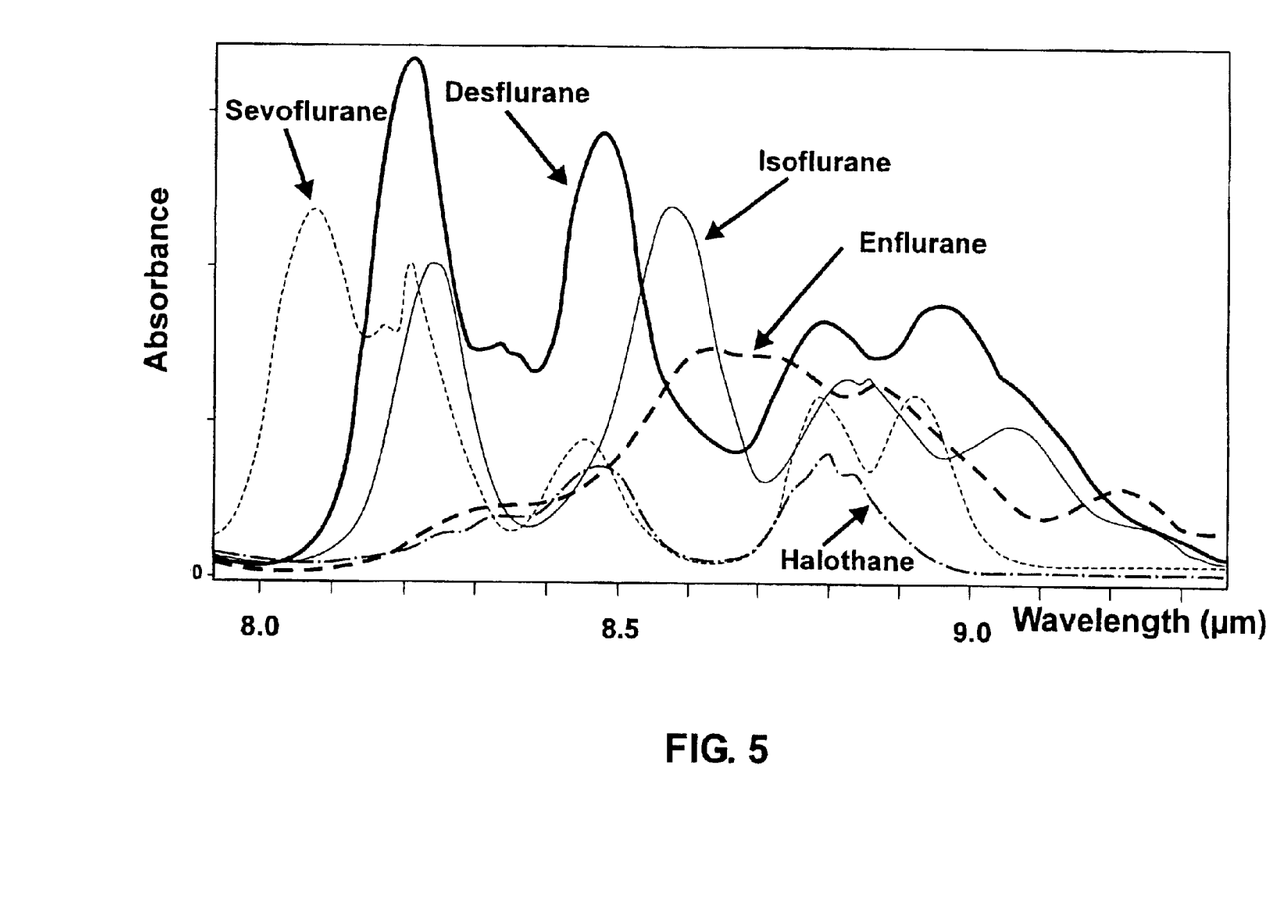
FIG. 5 presents the infrared absorbance of various anesthesia gases at the wavelength range of 7.9–9.5 $\mu$m.

FIG. 5 present the infrared absorbance of various gases, which are present in breathing air during anesthesia, as function of the wavelength of infrared radiation. The effect of halothane, for example, may be corrected by selecting the second wavelength range in a method according to the invention to cover the absorption band of halothane located at about 8.85 μm. Similarly, the effect of enflurane may be corrected using the absorption band located at about 9.3 μm. It may be also possible to correct the effect of some other gases using a method according to the invention.

Figure 6A:
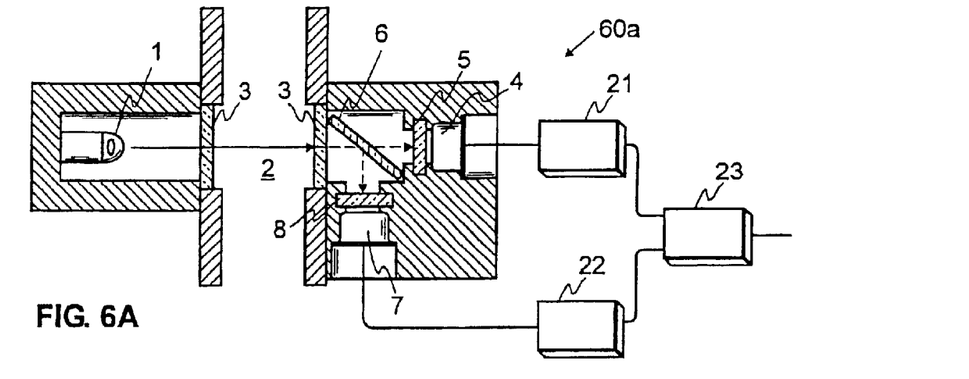
FIGS. 6A and 6B present schematic drawings of measurement arrangements according to fourth preferred embodiment of the invention.
Figure 6B:
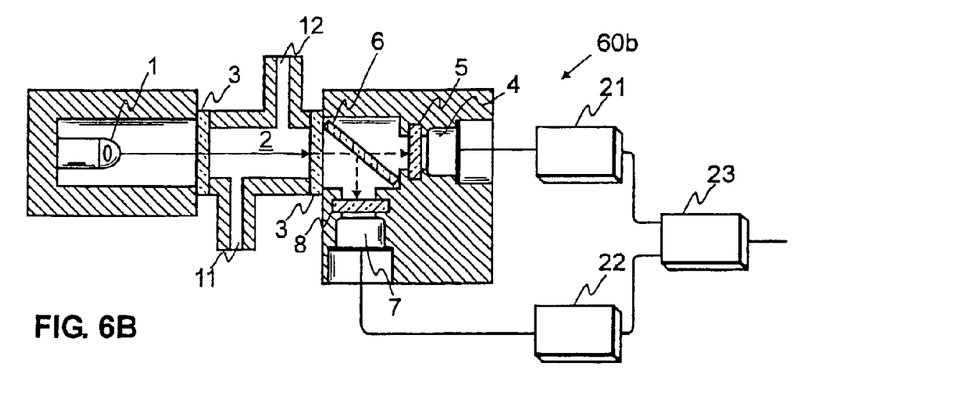

FIGS. 6A and 6B present schematic drawings of measurement arrangements 60a and 60b according to a fourth preferred embodiment of the invention. The difference between the measurement arrangements is the implementation of the sample gas chamber. The measurement arrangement 60a is a mainstream gas analyzer, where the sample gas container 2 is part of a tube carrying the alveolar exhalation air of a patient. The part of the tube forming the sample gas container 2 is determined by the position of the infrared radiation transparent windows 3. The measurement arrangement 60b is a sidestream gas analyzer, and the sample gas is provided to and from the sample gas container 2 via feeder tubes 11 and 12.

The measurement arrangements 60a and 60b contain a radiation source 1, which emits infrared radiation over a certain wavelength range, which covers the first and second transmission bands selected according to the invention. In measurement arrangements for determining the concentration of carbon dioxide in the presence of nitrous oxide, for example, the radiation source should emit infrared radiation at least over the wavelength range of 3.5–4.5 μm. The radiation source 1 may be, for example, a filament lamp, typically a tungsten lamp.

In measurement arrangements 60a and 60b, there are two radiation detectors 4 and 7, which are used to determine the first and second measurement signals $S_1(\Delta\lambda_1)$ and $S_1(\Delta\lambda_2)$ during measurements. The first radiation detector 4 is used, for example, to detect the intensity of radiation at the first transmission band, in other words the first measurement signal $S_1(\Delta\lambda_1)$ and the second radiation detector 8 is used to detect the intensity of radiation at the second transmission band. The measurement channel 21 is responsible, for example, for amplifying the first measurement signal and for performing an analog-to-digital conversion of the signal. Similarly, the measurement channel 22 is responsible for processing the second measurement signal. The concentration determination unit 23 is responsible for determining the concentration of the first gas component using a certain predetermined formula, a value of k and the signals provided by the measurement channels. The concentration determination unit 23 is typically at least partly implemented using software.

The transmission bands are defined by optical bandpass filters 5 and 8. A first filter 5 determines the first transmission band $\Delta\lambda_1$. The width of the first transmission band is typically about 100 nm, and the first transmission band is typically centered at a peak value of a transmission band related to the first gas component. The first filter may be, for example, an interference filter. A second filter 8 determines the second transmission band $\Delta\lambda_2$, whose width is typically a few tenths of a micrometer. The second filter may also be an interference filter. For example BARR Associates, Inc. produces interference filters which a suitable for measurement arrangements according to the invention. The radiation detectors 4 and 7 are such radiation detectors that they detect radiation at the first and second transmission bands, correspondingly. They may be, for example, thermocouples or thermopiles, which have a flat intensity response over a wide wavelength range. They may alternatively be some solid-state detectors.

It is possible to make the structure of the measurement arrangements 60a and 60b simpler by combining the optical bandpass filter 5 with the window of the radiation detector 4 and/or by combining the optical bandpass filter 8 with the window of the radiation detector 7, or using the optical filters as windows of the detectors.

A beam splitter 6 is used in the measurement arrangements 60a and 60b to divide the radiation beam, which has passed through the radiation transparent windows and the gas mixture sample, to the two detectors 4 and 7. The beam splitter 6 divides the radiation beam in a certain constant way to the detectors 4 and 7. The beam splitter may be, for example, a sapphire plate, and the wavelength distribution for the transmitted portion and for the reflected portion is substantially the same, whereupon the beam splitter 6 is a non-selective beam splitter.

Figure 7A:
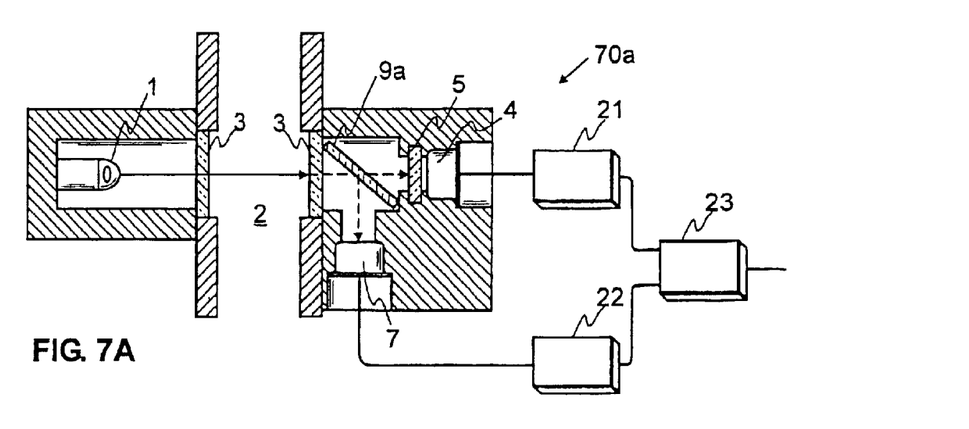
FIGS. 7A and 7B present schematic drawings of measurement arrangements according to fifth preferred embodiment of the invention.
Figure 7B:
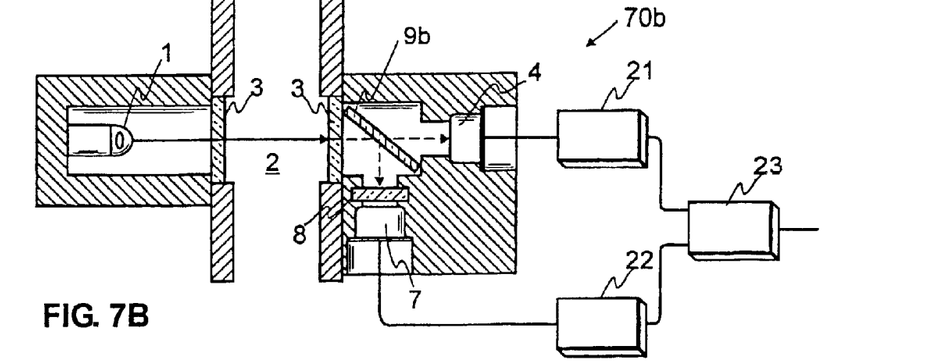

FIGS. 7A and 7B present measurement arrangements 70a and 70b according to a fifth preferred embodiment of the invention. Both the measurement arrangements 70a and 70b are illustrated as mainstream gas analyzers, but they may be implemented alternatively as sidestream gas analyzers. The measurement arrangements 70a and 70b contain a radiation source 1, a first detector 4 and a second radiation detector 7 similarly as the measurement arrangement 60a.

The difference between these measurement arrangements 70a and 70b according to the fifth preferred embodiment of the invention to the measurement arrangements 60a and 60b according to the fourth preferred embodiment of the invention is that here the beam splitter 9 is an optical filter that reflects/passes radiation at a certain wavelength range. In measurement arrangement 70a the beam splitter 9a reflects radiation at either the first or the second transmission band, so it may be called a blocking filter. FIG. 7A illustrates the case where radiation at the second transmission range is reflected. There is thus no need to further filter the reflected radiation incident on one of the detectors, the second detector 7 in FIG. 7A. The radiation that passes the beam splitter 9a is filtered either with an optical bandpass filter or with an optical high pass filter or with an optical low pass filter before it is incident on the detector which is behind the beam splitter 9a, a first bandpass filter 5 in FIG. 7A. So this kind of beam splitter is a selective beam splitter. In this case the transmission range of the optical first band pass filter 5 shall be included within the transmission range of the beam splitter 9, whereupon the second transmission wavelength range $\Delta\lambda_2$ of the beam splitter is substantially wider than the first transmission band or otherwise includes the first transmission band, or alternatively the first transmission wavelength range $\Delta\lambda_1$ of the beam splitter is substantially wider than the second transmission band or otherwise includes the second transmission band. If the beam splitter 9a reflects radiation at the second transmission range, the places of the detector 4 and 7 are changed compared to their places in FIG. 7A. The second bandpass filter 8 is, in this case, placed between the beam splitter 9a and the second detector 7.

In measurement arrangement 70b the beam splitter 9b passes radiation at the first or second transmission band, and therefore there is no need to further filter the radiation passing the beam splitter 9b and incident on one detector. The beam splitter is, for example, a transmission band filter, and acts simultaneously like the optical second band pass filter 8 as described earlier. The radiation that is reflected by the beam splitter 9b can contain all wavelengths but the transmitted wavelengths and therefore an optical bandpass filter is placed between the beam splitter 9b and the other detector, to which reflected radiation is incident. In FIG. 7B the beam splitter 9b passes radiation at the first transmission band, and the second transmission band filter is placed between the beam splitter 9b and the second detector 7. If the beam splitter 9b passes radiation at the first transmission band, the places of the first and second detector are switched compared to those presented in FIG. 7B.

Figure 8:
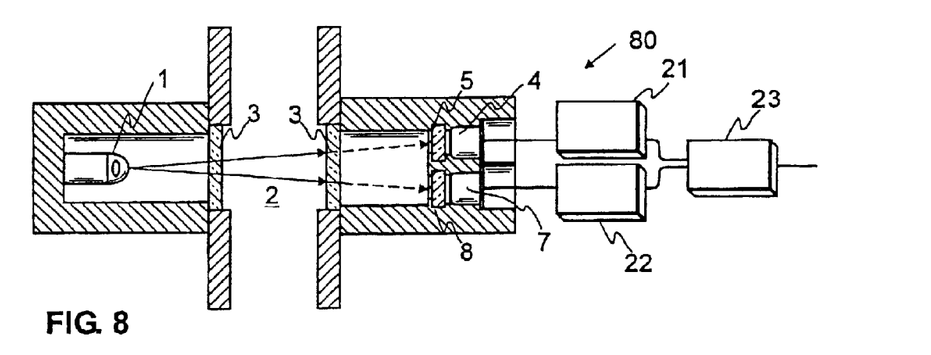
FIG. 8 presents a schematic drawing of a measurement arrangement according to a sixth preferred embodiment of the invention.

FIG. 8 presents a measurement arrangement 80 according to a sixth preferred embodiment of the invention. In the measurement arrangement 80 the first and second radiation detectors 4 and 7 are both directly facing the sample gas container 2. There is thus no need for a beam splitter. In a further embodiment of the invention the first and second radiation detectors are provided in one detector casing, comprising two separate independent detection areas. Dextex Research Center, Inc., for example, manufactures such detectors.

The composition of the gas mixture to be analyzed typically changes as a function of time, so to determine the concentration of the first gas component accurately, the signals obtained from the first and second detector need to be synchronized. In measurement arrangements 60a, 60b, 70a, 70b and 80 it is possible to determine the first and second measurement signal at a same time, and because the radiation incident on both the detectors 4 and 7 in these measurement arrangements passes along the same radiation path through the radiation transparent windows 3 and through the sample gas container 2, containing a certain gas mixture sample to be analyzed, the signals measured at a time correspond to the same gas mixture sample. The synchronization of the measurement signals is thus quite an easy task. Furthermore, because the first and second measurement signals can be measured continuously, it is possible to provide concentration of the first gas component in real time. For a real time surveillance of, for example, carbon dioxide concentration in a patient's breathing air the concentration can be determined, for example, at every 5–20 ms.

Figure 9:
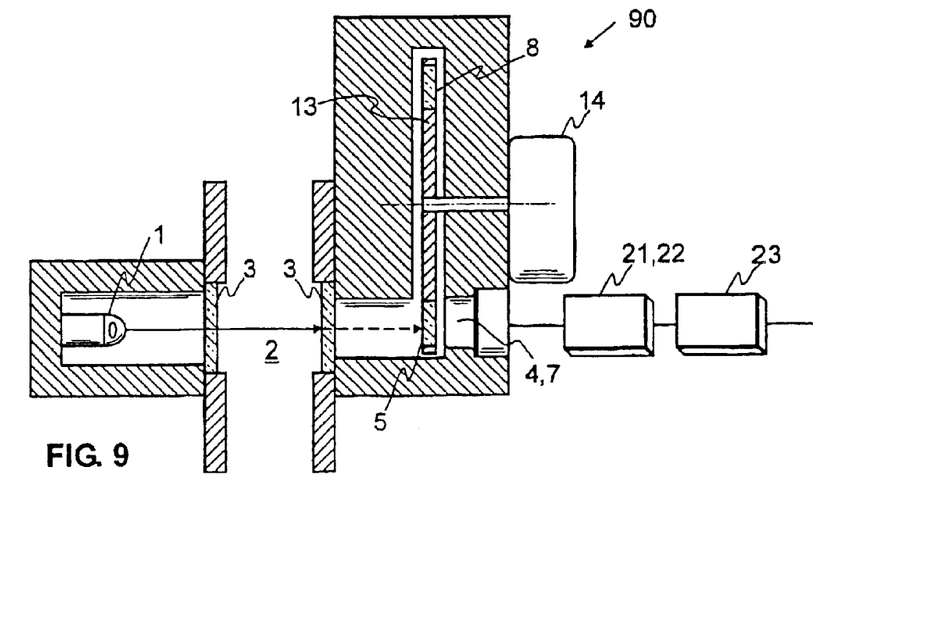
FIG. 9 presents a schematic drawing of a measurement arrangement according to a seventh preferred embodiment of the invention.

FIG. 9 presents a schematic drawing of a measurement arrangement 90 according to a seventh preferred embodiment of the invention. In this measurement arrangement there is one radiation detector 4, which is used to determine the first and second measurement signals $S_1(\Delta\lambda_1)$ and $S_1(\Delta\lambda_2)$. The optical bandpass filters 5 and 7 are placed to a filter wheel 13, which is rotated, for example, by a step motor 14. The first measurement signal is determined, when the first optical bandpass filter 5 is placed in front of the detector 4, and the second measurement signal is determined, when the second optical bandpass filter 7 is placed in front of the detector 4. Using this measurement arrangement it is not possible to measure the first and second measurement signals at precisely the same time. One advantage of the measurement arrangement 90 is, however, that a measurement signal corresponding to a situation where no radiation enters the detector 4 can be determined, for example, when switching the filters or by placing a plate, which passes no radiation, to one of the filter places in the filter wheel.

If there is need to determine a measurement signal corresponding to the situation, where no radiation enters the detector 4, a separate shutter can be added to the measurement arrangements presented in FIGS. 6–8.

In all measurement arrangements according to the invention, the first transmission band $\Delta\lambda_1$ is such that it is within an absorption band of the first gas component, whose concentration is to be determined, and the second transmission bands $\Delta\lambda_2$ is such that it is outside the absorption bands of the first gas component and it comprises a second absorption band of a second gas component possibly present in the gas mixture and having a collision broadening effect on the first gas component. The strength of the second absorption band is furthermore substantially less than the strength of the first absorption band.

Furthermore, in measurement arrangements according to preferred embodiments of the invention, the width of the second transmission band is selected so that the second measurement signal $S_2(\Delta\lambda_2)$, which is related to absorption of the second gas component and which is provided by the second radiation detector 7, or by the first radiation detector 4 with the second bandpass filter 8 placed in front of it, cancels out an effect, which is caused by the collision broadening affecting the first measurement signal $S_2(\Delta\lambda_1)$, on the concentration of the first gas component at least when the gas mixture to be analyzed contains a certain first concentration of the first gas component and a certain second concentration of the second gas component. The concentration is determined using a certain formula and using the first measurement signal $S_2(\Delta\lambda_1)$ and the second measurement signal $S_2(\Delta\lambda_2)$. To select the second transmission band, any method according to the invention may be used.

What is claimed:

1. A method for non-dispersive analysis of gas mixtures for determining the concentration of a first gas component in a gas mixture, the first gas component having absorbance properties which may be influenced by other gas components of said gas mixture, said method comprising the steps of:

(A) providing a radiation source emitting radiation over a wavelength range along a radiation path through the gas mixture;

(B) providing to said radiation path a first optical bandpass filter having a first transmission band within an absorption band of said first gas component;

(C) detecting a first intensity of radiation that has passed along said radiation path and through said first optical bandpass filter, the first intensity of radiation producing a first measurement signal when the gas mixture in the radiation path is the gas mixture to be analyzed;

(D) providing to said radiation path a second optical bandpass filter having a second transmission band;

(E) detecting a second intensity of radiation that has passed along said radiation path and through said second optical bandpass filter, the second intensity of radiation producing a second measurement signal when the gas mixture in the radiation path is the gas mixture to be analyzed;

(F) determining a concentration value for the first gas component in the gas mixture to be analyzed using a predetermined formula or predetermined formulas, employing as inputs at least said first measurement signal and said second measurement signal; and (G) selecting the second transmission band so that it is substantially or entirely outside the absorption bands of said first gas component and so that it comprises an absorption band of a certain second gas component causing a distortion in the absorption band of said first gas component, the radiation absorption occurring in the absorption band of the second gas component being substantially less than the radiation absorption occurring in the absorption band of the gas component.

2. A method of claim 1, further comprising the step of:

(H) selecting the width of the second transmission band so that the second measurement signal, related to absorption of the second gas component, corrects a deviation in a determined concentration value of the first gas component, which deviation is caused by said distortion affecting the first measurement signal, at least when the gas mixture to be analyzed contains a certain first concentration of the first gas component and a certain second concentration of the second gas component.

3. A method of claim 2, wherein said step (H) of selecting the width of the second transmission band comprises the substeps of:

(a) estimating a first calibration signal, which is the first measurement signal corresponding to a calibration gas mixture having the first concentration of the first gas component and the second concentration of the second gas component, and a second calibration signal, which is the second measurement signal corresponding to the calibration gas mixture;

(b) estimating the concentration of the first gas component in the calibration gas mixture using said formula and the first and second calibration signals and a ratio of the first calibration signal and the second calibration signal; and (c) approving the selection of the second transmission bandwidth, if the estimated concentration of the first gas component in the calibration gas mixture is substantially equal to the first concentration.

4. A method of claim 3, wherein the substep (a) of estimating the first calibration signal comprises the substeps of:

(a1) providing in said radiation path a calibration gas mixture having the first concentration of the first gas component and the second concentration of the second gas component; and (a2) producing with a first detector the first calibration signal and with a second detector the second calibration signal.

5. A method of claim 3, further comprising the step (I) with substeps of:
- (d) selecting an initial second transmission band before providing the calibration gas mixture;
- (e) providing the calibration gas mixture and producing the first and second calibration signals; and
- (f) selecting a new width for the second transmission band, if the second transmission band is not that approved in substep (c); and where after carrying out substep (d) the substeps (a), (b), (c), (e) and (f) are repeated in the following order: (e), (a), (b), (c), (f) until the second transmission band corresponds to that approved in substep (c).

6. A method of claim 1, wherein the intensity of radiation is detected at a same time in the first transmission band and in the second transmission band using separate first and second detectors.

7. A method of claim 1, wherein the detecting steps are carried out with a common detector and the intensity of radiation is detected alternately in the first transmission band and in the second transmission band by alternating the provision of the first bandpass filter and the second bandpass filter in the radiation path.

8. A method of claim 1, wherein the first gas component is carbon dioxide and the second gas component is nitrous oxide.

9. A method according to claim 8, wherein the first transmission band is substantially centered at 4.3 $\mu$m, and the width of the first transmission band is substantially 100 nm, and the second transmission band is substantially at 3.5 $\mu$m–4.0 $\mu$m.

10. A method of claim 8, utilized for determining the concentration of carbon dioxide in a gas mixture comprising the respiratory breathing gases of a subject.

11. A method of claim 10, utilized for determining the concentration of carbon dioxide in a gas mixture comprising the alveolar exhalation breathing gases of the subject.

12. A method of claim 1, wherein said distortion is a collision broadening.

13. A method for non-dispersive analysis of gas mixtures for determining the concentration of a first gas component in a gas mixture, the first gas component having absorbance properties which may be influenced by other gas components of said gas mixture, said method comprising the steps of:
- (A) providing a radiation source emitting radiation over a wavelength range along a radiation path through the gas mixture;
- (B) providing to said radiation path a first extension radiation path with a first optical bandpass filter having a first transmission band within an absorption band of said first gas component;
- (C) detecting a first intensity of radiation passing along said radiation path and said first extension radiation path, the first intensity of radiation producing a first measurement signal when the gas mixture in the radiation path is the gas mixture to be analyzed;
- (D) providing to said radiation path a selective beam splitter having a transmission range, which comprises at least the first transmission band;
- (E) providing to said radiation path a second extension radiation path with an unlimited transmission;
- (F) detecting a second intensity of the radiation passing along said radiation path and said second extension radiation path, the second intensity producing a second measurement signal when the gas mixture in the radiation path is the gas mixture to be analyzed;
- (G) determining a concentration value for the first gas component in the gas mixture to be analyzed using a predetermined formula or predetermined formulas, employing as inputs at least said first measurement signal and said second measurement signal; and
- (H) selecting the transmission range so that it extends substantially or entirely outside the absorption bands of said first gas component and so that it comprises an absorption band of a certain second gas component causing a distortion in the absorption band of said first gas component, the radiation absorption occurring in the absorption band of the second gas component being substantially less than the radiation absorption occurring in of the absorption band of the first gas component.

14. A method of claim 13, further comprising the step of:
- (I) selecting at least one of the frequency spectrum position and transmission range width characteristics of the transmission range so that the second measurement signal, related to absorption of the second gas component, corrects a deviation in a determined concentration value of the first gas component, which deviation is caused by said distortion affecting the first measurement signal, at least when the gas mixture to be analyzed contains a certain first concentration of the first gas component and a certain second concentration of the second gas component.

15. A method of claim 14, wherein said step (I) of selecting at least one of the frequency spectrum position and transmission range width characteristics of the transmission range comprises the substeps of:
- (a) estimating a first calibration signal, which is the first measurement signal corresponding to a calibration gas mixture having the first concentration of the first gas component and the second concentration of the second gas component, and a second calibration signal, which is the second measurement signal corresponding to the calibration gas mixture;
- (b) estimating the concentration of the first gas component in the calibration gas mixture using said formula and the first and second calibration signals and a ratio of the first calibration signal and the second calibration signal
- (c) approving the characteristics of the transmission range, if the concentration of the estimated first gas component in the calibration gas mixture is substantially equal to the first concentration.

16. A method of claim 15, wherein the substep (a) of estimating the first calibration signal comprises the substeps of:
- (a1) providing in said radiation path a calibration gas mixture having the first concentration of the first gas component and the second concentration of the second gas component; and
- (a2) producing with a first detector a first calibration signal and with a second detector a second calibration signal.

17. A method of claim 15, further comprising the step (J) with substeps of:
- (d) selecting an initial transmission range before providing the calibration gas mixture;
- (e) providing the calibration gas mixture and producing the first and second calibration signals; and
- (f) selecting a new characteristic for the transmission range, if the second transmission band is not that approved in substep (c); and where after carrying out substep (d) the substeps (a), (b), (c), (e) and (f) are repeated in the following order: (e), (a), (b), (c), (f) until characteristics of the second transmission band correspond to that approved in substep (c).

18. A method of claim 13, wherein the intensity of radiation is detected at a same time in the first transmission band and in the second transmission band using separate first and second detectors.

19. A method of claim 13, wherein the first gas component is carbon dioxide and the second gas component is nitrous oxide.

20. A method of claim 19, wherein the first transmission band is substantially centered at 4.3 µm and has a width of substantially 100 mm.

21. A method of claim 19, utilized for determining the concentration of carbon dioxide in a gas mixture comprising the respiratory breathing gases of a subject.

22. A method of claim 21, utilized for determining the concentration of carbon dioxide in a gas mixture comprising the alveolar exhalation breathing gases of the subject.

23. A method of claim 13, wherein said distortion is a collision broadening.

24. An apparatus for providing an indication of the concentration of a first gas component in a mixture of gases, said apparatus employing non-dispersive absorption measurement of radiation and comprising:
    a sample chamber for containing the gas mixture;
    a radiation source for transmitting radiation through the gas mixture;
    a first optical transmission band filter and radiation detector means for detecting the intensity of the radiation exiting the sample chamber in a first transmission band, which comprises an absorption band of the first gas component;
    a second optical transmission band filter and radiation detector means for detecting the intensity of the radiation exiting the sample chamber in a second transmission band; and
    concentration determination means arranged to determine the concentration of the first gas component in the gas mixture using a certain concentration formula or formulas and using the detected intensity of the radiation in the first transmission band and in the second transmission band, the second transmission band being substantially or entirely outside the absorption bands of said first gas component and comprising an absorption band of a certain second gas component causing a distortion in the absorption band of the first gas component, the radiation absorption occurring in the absorption band for the second gas component being substantially less than the radiation absorption occurring in the absorption band for the gas component.

25. An apparatus of claim 24, wherein said radiation detector means has a sensor area of a first radiation detector and a sensor area of a second radiation detector formed as separate units and directed toward the sample chamber.

26. An apparatus of claim 25, wherein the first radiation detector and the second radiation detector are housed within a single detector casing.

27. An apparatus of claim 25, wherein one of the optical transmission band filters is arranged at a certain angle so that it operates as a beam splitter transmitting radiation in the transmission band defined by one of said optical transmission band filters to one of the radiation detectors and reflecting radiation at least in the other transmission band towards the other of said radiation detectors.

28. An apparatus of claim 27, wherein the first transmission band filter is arranged to operate as a beam splitter.

29. An apparatus of claim 27, wherein the second transmission band filter is arranged to operate as a beam splitter.

30. An apparatus of claim 25, wherein the sensor area of first radiation detector and the sensor area of the second radiation detector are substantially parallel to each other.

31. An apparatus of claim 24, wherein said radiation detector means for said first and second transmission band filters comprise a common detector with a single and common sensor area, which is directed toward the sample chamber, and the first transmission band filter and the second transmission band filter are arranged in a movable filter changing means.

32. An apparatus of claim 24, further comprising beam division means splitting the radiation substantially wavelength-independently towards a first radiation detector and a second radiation detector.

33. An apparatus of claim 24, wherein the first transmission band is substantially centered at 4.3 µm and the width of the first transmission band is substantially 100 nm, and the second transmission band is substantially at 3.5 µm–4.0 µm.

34. An apparatus for providing an indication of the concentration of a first gas component in a mixture of gases, said apparatus employing non-dispersive absorption of radiation and comprising:
    a sample chamber for containing the gas mixture;
    a radiation source for transmitting radiation through the gas mixture;
    first radiation detector for detecting the intensity of the radiation exiting the sample chamber in a first wavelength range, which comprises an absorption band of the first gas component;
    a second radiation detector for detecting the intensity of the radiation exiting the sample chamber in a second wavelength range, which is substantially or entirely outside the first wavelength range;
    an optical transmission band filter, whose transmission band is one of the first and second wavelength ranges;
    concentration determining means arranged to determine the concentration of the first gas component in the gas mixture using a certain concentration formula and using the detected intensity of the radiation in the first wavelength range and in the second wavelength range; and
    an optical blocking range filter, the blocking range of which comprises at least the other of the first and second wavelength ranges and which is arranged at a certain angle so that it operates as a wavelength selective beam splitter reflecting radiation in the blocking range to one of the radiation detectors and transmitting radiation at least at the transmission band of the optical transmission band filter towards the other radiation detector,
    the second wavelength range being substantially outside the absorption bands of said first gas component and so that it comprises an absorption band of a certain second gas component causing a distortion in the absorption band of the first gas component, the radiation absorption occurring in the absorption band for the second gas component being substantially less than the radiation absorption occurring in the absorption band for the first gas component.

35. An apparatus of claim 34, wherein the optical blocking range filter operating as a wavelength selective beamsplitter reflects radiation within the first wavelength range to the first radiation detector and transmits other wavelength ranges to an optical bandpass filter that transmits radiation within the second wavelength range to the second radiation detector.

36. An apparatus of claim 34, wherein the optical blocking range filter operating as a wavelength selective beamsplitter reflects radiation within the second wavelength range to the second radiation detector and transmits other wavelength ranges to an optical bandpass filter that transmits radiation within the first wavelength range to the first radiation detector.

37. An apparatus of claim 34, wherein the first transmission band is substantially centered at 4.3 $\mu$m and the width of the first transmission band is substantially 100 nm, and the second transmission band is substantially at 3.5 $\mu$m–4.0 $\mu$m.

38. An apparatus of claim 34, wherein the blocking range of the optical blocking range filter has a width or sub-ranges including both the first wavelength range and the second wavelength range.

* * * * *